United States Patent
Pugh et al.

(10) Patent No.: US 9,289,623 B2
(45) Date of Patent: Mar. 22, 2016

(54) METHOD AND DEVICE FOR MONITORING AND TREATMENT OF SEASONAL AFFECTIVE DISORDER

(71) Applicant: Johnson & Johnson Vision Care, Inc., Jacksonville, FL (US)

(72) Inventors: Randall B. Pugh, Jacksonville, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 152 days.

(21) Appl. No.: 13/833,196

(22) Filed: Mar. 15, 2013

(65) Prior Publication Data

US 2014/0277291 A1    Sep. 18, 2014

(51) Int. Cl.
*A61N 5/06* (2006.01)
*G02C 7/04* (2006.01)
*A61B 5/145* (2006.01)
*A61B 5/16* (2006.01)
*A61B 5/00* (2006.01)

(52) U.S. Cl.
CPC .......... *A61N 5/0618* (2013.01); *A61B 5/14507* (2013.01); *A61B 5/14546* (2013.01); *A61B 5/165* (2013.01); *A61B 5/6821* (2013.01); *A61N 5/06* (2013.01); *G02C 7/04* (2013.01); *A61B 5/002* (2013.01); *A61B 5/4836* (2013.01); *A61B 2560/0214* (2013.01); *A61N 2005/0648* (2013.01); *A61N 2005/0652* (2013.01)

(58) Field of Classification Search
None
See application file for complete search history.

(56) References Cited

U.S. PATENT DOCUMENTS

| | | | | |
|---|---|---|---|---|
| 4,014,321 A * | 3/1977 | March | ................ | A61B 5/14558 356/39 |
| 4,485,820 A * | 12/1984 | Flower | ............... | A61B 5/14555 351/219 |
| 5,830,139 A * | 11/1998 | Abreu | .......................... | 600/405 |
| 6,221,028 B1 * | 4/2001 | Lieberman | ............... | A61B 3/14 351/200 |
| 6,299,632 B1 * | 10/2001 | Jaillet | ............................ | 607/88 |
| 6,350,275 B1 * | 2/2002 | Vreman et al. | ................. | 607/88 |
| 6,681,127 B2 * | 1/2004 | March | ......................... | 600/319 |
| 6,790,178 B1 * | 9/2004 | Mault et al. | .................. | 600/300 |
| 7,108,680 B2 * | 9/2006 | Rohr et al. | .................... | 604/151 |

(Continued)

FOREIGN PATENT DOCUMENTS

WO  WO 0025662 A1  5/2000
WO  WO 2012106542 A  8/2009

OTHER PUBLICATIONS

EP Search Report EP 14 15 9743 Date of Completion Oct. 22, 2014.

(Continued)

*Primary Examiner* — Lynsey Crandall
*Assistant Examiner* — Manolis Pahakis

(57) ABSTRACT

This invention provides for an energized biomedical ophthalmic device and associated method of measuring changes in biomarkers contained in tear film to generate data related to a light therapy regimen used to treat symptoms associated with seasonal affective disorder. In some embodiments, the energized biomedical ophthalmic device can include an energized contact lens with a light source in communication with a processor controlling said light source according to the light therapy regimen. The light therapy regimen may be generated or modified by the processor from the measured changes and sometimes from user's preferences, and/or additional measurements, including for example, light exposure and/or circadian rhythm of the user.

11 Claims, 10 Drawing Sheets

(56) References Cited

U.S. PATENT DOCUMENTS

| | | | |
|---|---|---|---|
| 7,187,960 B2* | 3/2007 | Abreu | 600/310 |
| 7,321,795 B2* | 1/2008 | Bogdanowicz | A61N 1/32 351/159.02 |
| 2005/0059977 A1* | 3/2005 | Borjigin | 606/80 |
| 2005/0175505 A1* | 8/2005 | Cantor et al. | 422/68.1 |
| 2005/0278003 A1* | 12/2005 | Feldman | 607/88 |
| 2006/0136018 A1* | 6/2006 | Lack et al. | 607/88 |
| 2007/0002470 A1* | 1/2007 | Domschke et al. | 359/819 |
| 2007/0168000 A1* | 7/2007 | Happawana et al. | 607/88 |
| 2008/0004905 A1* | 1/2008 | Jung et al. | 705/2 |
| 2008/0091119 A1* | 4/2008 | Moffitt | 600/551 |
| 2009/0005833 A1* | 1/2009 | Cameron et al. | 607/45 |
| 2009/0326616 A1* | 12/2009 | Aarts et al. | 607/88 |
| 2010/0001926 A1* | 1/2010 | Amirparviz et al. | 345/7 |
| 2010/0292629 A1* | 11/2010 | Dacey et al. | 604/8 |
| 2011/0152759 A1* | 6/2011 | Clymer et al. | 604/93.01 |
| 2011/0224502 A1* | 9/2011 | Herbst | G06F 19/345 600/301 |
| 2012/0016174 A1* | 1/2012 | De Taboada et al. | 600/2 |
| 2012/0041520 A1* | 2/2012 | Colbaugh | A61N 5/0618 607/88 |
| 2012/0095534 A1* | 4/2012 | Schlangen et al. | 607/90 |
| 2012/0199995 A1 | 8/2012 | Pugh | |
| 2012/0203310 A1* | 8/2012 | Pugh et al. | 607/93 |
| 2012/0215291 A1* | 8/2012 | Pugh et al. | 607/93 |
| 2012/0245444 A1* | 9/2012 | Otis | A61B 5/1486 600/345 |

OTHER PUBLICATIONS

Singapore Search Report for Application 10201400483T Date of the Written Opinion Sep. 18, 2015; Date of actual completion of the search: Jun. 11, 2015.

* cited by examiner

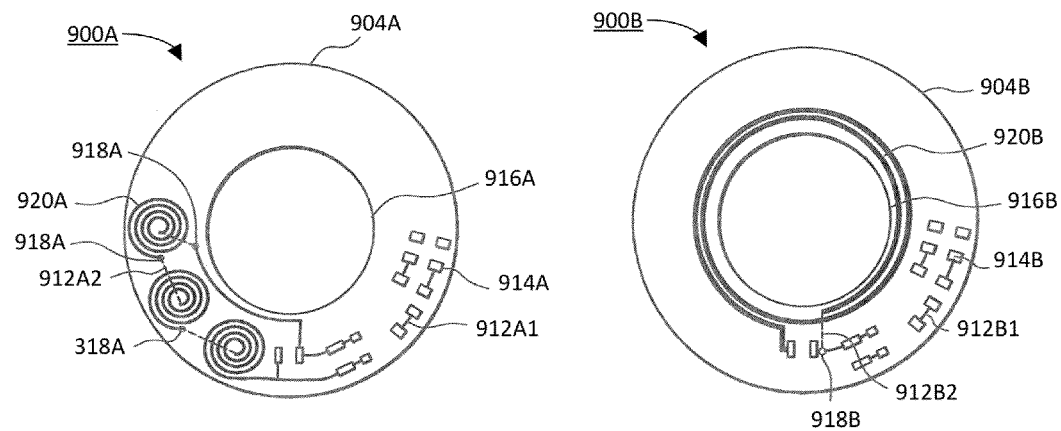
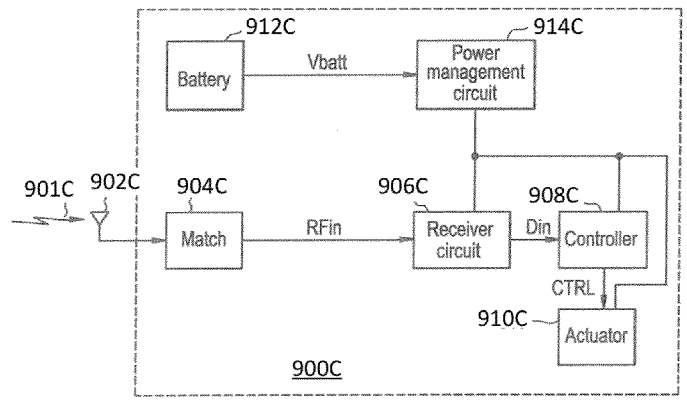
Figs. 9A, 9B, & 9C

METHOD AND DEVICE FOR MONITORING AND TREATMENT OF SEASONAL AFFECTIVE DISORDER

FIELD OF USE

The present invention relates to devices and methods used to diagnose and treat seasonal affective disorder (SAD). More specifically, to energized biomedical ophthalmic devices capable of monitoring SAD symptoms for light therapy treatments.

BACKGROUND OF THE INVENTION

Seasonal affective disorder (SAD) is a well-established mood disorder wherein sufferers experience depressive symptoms in a certain season of the year, most frequently during the winter months. Those affected by SAD often have normal mental health during most of the year. Symptoms of SAD may include, but are not limited to, excessive sleeping, lack of energy, craving carbohydrates, difficulty concentrating, and withdrawal from social activities. The symptoms result in feelings of depression, hopelessness, pessimism, and lack of pleasure.

Seasonal mood variations are believed to be related to changes in exposure to light. Individuals in geographic areas, such as the Arctic region, that experience fewer daylight hours, lower sunlight intensity, or significant periods of overcast skies exhibit a greater incidence of SAD. Variations in prevalence of SAD within the adult population are evident within the United States, ranging from low rates in Florida and other sunny states to notably higher rates in Alaska, New Hampshire and other northern or overcast areas.

Light therapy has been researched and established as a prominent and effective treatment for classic, or winter-based, seasonal affective disorder. Conventional light therapy employs a device which emits significantly more lumens than a standard incandescent lamp. Common implementations include the preferred bright white full spectrum light at 10,000 lux, or optionally blue light at a wavelength of 480 nm at 2,500 lux, or green light at a wavelength of 500 nm at 350 lux. Light therapy normally requires a patient to sit with their eyes open at a prescribed distance from the light source for thirty to sixty minutes each day. This seasonal treatment is maintained for several weeks until the patient experiences frequent exposure to natural light. A majority of patients find the existing therapy inconvenient and a considerable percentage, in some studies up to 19%, therefore stop the treatment. New methods and approaches are therefore desirable to deliver light therapy in more convenient, controlled, and intelligent manners.

SUMMARY OF THE INVENTION

The foregoing needs are met, to a great extent, by the present invention, wherein in one aspect it provides for an Energized Biomedical Ophthalmic Device capable of testing small volumes of tear fluid to monitor and provide Intelligent Light Therapy to treat SAD. Included in this description are a disclosure of a method to monitor SAD and deliver Intelligent Light Therapy accordingly, and an Energized Biomedical Ophthalmic Device with a biomarker sensor used to monitor SAD symptoms and in logical communication with a Light Source. In some embodiments, the Energized Biomedical Ophthalmic Device can be an Energized Ophthalmic Lens comprising one or more sensor(s) and an integrated Light Source capable of treating SAD. In alternative embodiments, the Energized Ophthalmic Lens can comprise one or more sensor(s) and communication means to transfer sensor measured data to a controller in communication with a non-integrated Light Source capable of treating SAD.

In some aspects of the present invention, a personalized dosing regimen of Light Therapy can be achieved. The personalized dosing regimen can result in Intelligent Light Therapy when various data is analyzed to make compensation to the Programmed Therapy Schedule. Data analyzed can include, but is not limited to, sensor measured data relating to changes in biomarkers in the tear film of the Energized Biomedical Ophthalmic Device user. Compensations can include shifting treatment frequencies, durations, and/or light intensities to provide more effective treatment, while taking into account user's preferences, to provide a more positive experience to the user.

In some embodiments, monitoring of biomarkers may be achieved through one or more electrochemical sensor(s) with analytical sensitivity and contained in the Biomedical Ophthalmic Device. The electrochemical sensor(s) can analyze biomarkers in tear film including, for example, the presence and/or concentrations of symptom correlated biomolecules. Biomolecules interrelated to various symptoms of SAD can include but are not limited to: Serotonin, Melatonin, and Interleukin-6 Analysis of biomolecules may occur at predetermined frequencies or times of the day, for example, every hour, or three hours, or during specific activities, or times of the day when the user is most susceptible to experience SAD symptoms. Other sensors that can help monitor SAD symptoms may also be included by some embodiments, including for example, light sensors, or sensors capable of sensing changes in the circadian rhythm of the user.

According to some embodiments, the sensors can be a microchip with electrophoresis and selective chemoluminescence analytical sensitivity capabilities. In some preferred sensors, the analytical sensitivity may be achieved through an energized microchip component that can measure and data from the tear film biomolecules, for example, one or more of: electrical conductance, resistance or capacitance; changes in fluorescence, absorbance, light scatter or plasmon resonance, light exposure, and circadian rhythm, to monitor, diagnose, and/or provide Intelligent Light Therapy to treat SAD.

BRIEF DESCRIPTION OF THE DRAWINGS

FIG. 9A illustrates an energized biomedical ophthalmic device comprising an exemplary coil type of antenna according to some ophthalmic lens embodiments of the present invention.

FIG. 9B illustrates an energized biomedical ophthalmic device comprising an exemplary spiral type of antenna according to some contact lens embodiments of the present invention.

FIG. 9C is a block diagram representation of an antenna and receiver circuit in accordance to some embodiments of the present invention.

DETAILED DESCRIPTION OF THE INVENTION

Figure 1:
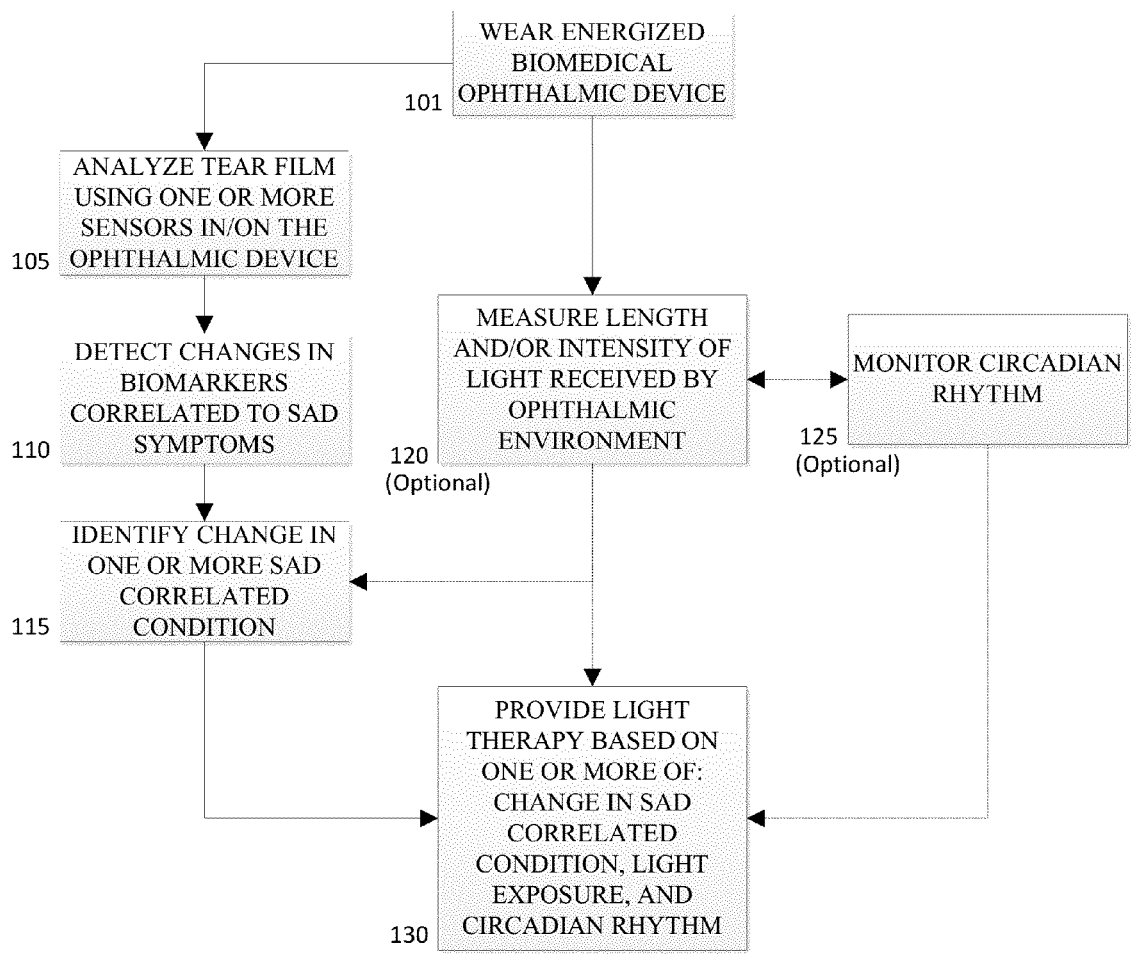
FIG. 1 illustrates method steps that may be used to implement some aspects of the present invention.

The present invention includes methods and an Energized Biomedical Ophthalmic Device for monitoring SAD symptoms and controlling light therapy used to treat SAD. In particular, the present invention includes methods and device embodiments that are capable of monitoring biomarkers in tear film, and/or ocular surface conditions and characteristics correlated to symptoms of SAD to provide Intelligent Light Therapy.

In the following sections detailed descriptions of embodiments of the invention will be given. The description of both preferred and alternative embodiments are exemplary embodiments only, and it is understood that to those skilled in the art variations, modifications and alterations will be apparent. It is therefore to be understood that said exemplary embodiments do not limit the scope of the underlying invention.

GLOSSARY

In this description directed to the present invention, various terms may be used for which the following definitions may apply:

"Biomedical Ophthalmic Device" refers to any ophthalmic device that is capable of residing in or on the eye. These devices can provide one or more of: optical correction, therapy, and may be cosmetic. For example, the biomedical ophthalmic device can refer to an energized contact lens, intraocular lens, overlay lens, ocular insert, optical insert, punctal plug, or other similar ophthalmic device through which vision is corrected or modified, an eye condition can be enhanced or prevented, and/or through which eye physiology is cosmetically enhanced (e.g., iris color). In some embodiments, the biomedical ophthalmic device of the invention can include soft contact lenses made from silicone elastomers or hydrogels, which include but are not limited to silicone hydrogels, and fluorohydrogels.

"Component" as used herein refers to a device which draws electrical current from an Energy Source to perform one or more of a change of logical state or physical state.

"Energized" as used herein refers to the state of being able to supply electrical current to or to have electrical energy stored within.

"Energy Harvesters" as used herein refers to a device capable of extracting energy from the environment and converting it to electrical energy.

"Energy Source" as used herein refers to a device capable of supplying Energy or placing a biomedical device in an Energized state.

"Energy" as used herein refers to the capacity of a physical system to do work. Many uses within this invention may relate to the said capacity being able to perform electrical actions in doing work.

"Intelligent light therapy" as used herein may refer to a method of delivering light therapy whereby a processor evaluates various data and, based on data analysis, dynamically makes compensating adjustments to a programmed light therapy schedule and/or function. Intelligent light Therapy can occur, for example, by adjusting light therapy based on one or more conditions, including but not limited to, the user's exposure to ambient light, measured biomarkers in tear film, and monitored circadian rhythm.

"Light Source" as used herein refers to a device capable of emitting light.

"Light therapy" as used herein refers to exposure to specific wavelengths of light, controlled with various devices, and administered for a specified amount of time, at a specified intensity and, in some cases, at a specified time of day.

"Lithium Ion Cell" refers to an electrochemical cell where Lithium ions move through the cell to generate electrical energy. This electrochemical cell, typically called a battery, may be reenergized or recharged in its typical forms.

"Lux" as used herein refers to units of illumination in the International System of Units (SI). Lux provides a measure of luminous power per area. One lux is the amount of illumination provided when one lumen is evenly distributed over an area of one square meter. This is also equivalent to the illumination that would exist on a surface from all points of which are one meter from a point source of one international candle. One lux is equal to 0.0929 foot-candle.

"Optical Zone" as used herein refers to an area of an ophthalmic lens through which a wearer of the ophthalmic lens sees.

"Power" as used herein refers to work done or energy transferred per unit of time.

"Programmed light therapy schedule" as used herein refers to a set of automated instructions that controls light therapy timing, duration and intensity based on variables such as measured data, dates, geographic region, and severity of a user's seasonal affective disorder symptoms. A programmed light therapy schedule may be set by an eye care professional, a medical doctor, a software code incorporated in a processor, and/or a user.

"Rechargeable or Re-energizable" as used herein refers to a capability of being restored to a state with higher capacity to do work. Many uses within this invention may relate to the capability of being restored with the ability to flow electrical current at a certain rate for a certain, reestablished time period.

"Reenergize or Recharge" as used herein refers to restoring to a state with higher capacity to do work. Many uses within this invention may relate to a restoring device with the capability to flow electrical current at a certain rate for a certain, reestablished time period.

"Seasonal Affective Disorder (SAD)" as used herein it may refer to a recurrent state of mood altering symptoms, usually experienced by people due to lack of sunlight, or light at certain wavelengths. It may include a mood disorder that occurs during seasons when exposure to sunlight is limited, characterized by symptoms of depression and relieved by the arrival of spring or by light therapy.

Humans' eyes, like other mammalian eyes, contain a fluid coating known as tear fluid. Tear fluid can hydrate and lubricate the ocular surface, protect it, and generally provides an adequate environment for ocular health and vision. Like blood and saliva, components of tear fluid including some protein biomolecules can come from diverse sources and may vary in concentrations according to physiological factors and/or environmental surrounding factors. The ability to measure biomolecules' characteristics, such as, concentrations, can provide helpful information for identifying, correlating conditions and symptoms, and/or monitoring optimum levels, for health management and intervention.

Protein biomolecules in tear fluid may be analyzed using methods including electrophoresis, microfluidic chip based systems, spectrometry, and liquid chromatography. However, tear fluid collection has presented challenges including the collection of small volumes for testing and preventing contamination in ways that are relatively innocuous to the individual, particularly due to the pronounced sensitivity of most healthy eyes. The present invention provides for methods and Energized Biomedical Ophthalmic Devices that can analyze biomolecules and, more specifically, biomolecules with identified proteins correlated to conditions or symptoms, also known as biomarkers.

Referring now to FIG. 1, method steps that may be used to monitor SAD related symptoms are illustrated. At 101, one or more energized Biomedical Ophthalmic Device(s) can be worn by an individual. An energized Biomedical Ophthalmic Device can reside in or on the eye. Some Biomedical Ophthalmic Devices are preferably placed on the anterior ocular surface and may be used to provide one or more of: optical correction, therapy, and may be cosmetic. For example, it may be an energized ophthalmic lens or energized ophthalmic device, including but not limited to a contact lens, intraocular lens, overlay lens, ocular insert, optical insert, punctal plug, or other similar ophthalmic device through which vision can be corrected or modified, an eye condition can be enhanced or prevented, and/or through which eye physiology can be enhanced cosmetically.

In some aspects of the present invention, the Energized Biomedical Device may be used to monitor one or more SAD related symptoms. Monitoring of the symptoms may take place through the analysis of biomarkers in tear film through the use of sensors comprised by the Energized Biomedical Ophthalmic Device. Additionally or alternatively, in some embodiments, it may also include measuring length and/or intensity of light received by the ophthalmic environment of the user 120, and/or monitoring the circadian rhythm 125 of the user.

When analysis of biomarkers in tear film through the use of sensors takes place 105, the biomarkers' changes can be correlated to known SAD symptoms 110. Examples of correlated symptoms of SAD may include, but are not limited to, excessive sleeping, lack of energy, craving carbohydrates, difficulty concentrating, and withdrawal from social activities. These symptoms can often result in feelings of depression, hopelessness, pessimism, and lack of pleasure which can be correlated to changes in specific tear film biomarkers. Changes in biomarker of tear film can include, but are not limited to, variations in serotonin levels and genetic polymosphisms, melatonin concentration changes signaling a phase change in circadian rhythm, and increased levels of Interleukin-6.

Known levels and thresholds of biomarkers concentrations in tear film related to SAD may pre-programmed into a Component of the device used for the monitoring and, additionally or alternatively, the device may continue to learn from inputs and collected data particular to the user. In addition, because concentrations may vary with factors, such as, age and environmental conditions, normal values measured in blood, serum or saliva analytes of the individual, or of a comparable population, may be correlated to tear film values of the user. The changes or determined values then may be monitored 115 and light therapy based on the changes may be provided to the user 130 when it is needed.

Figure 2:
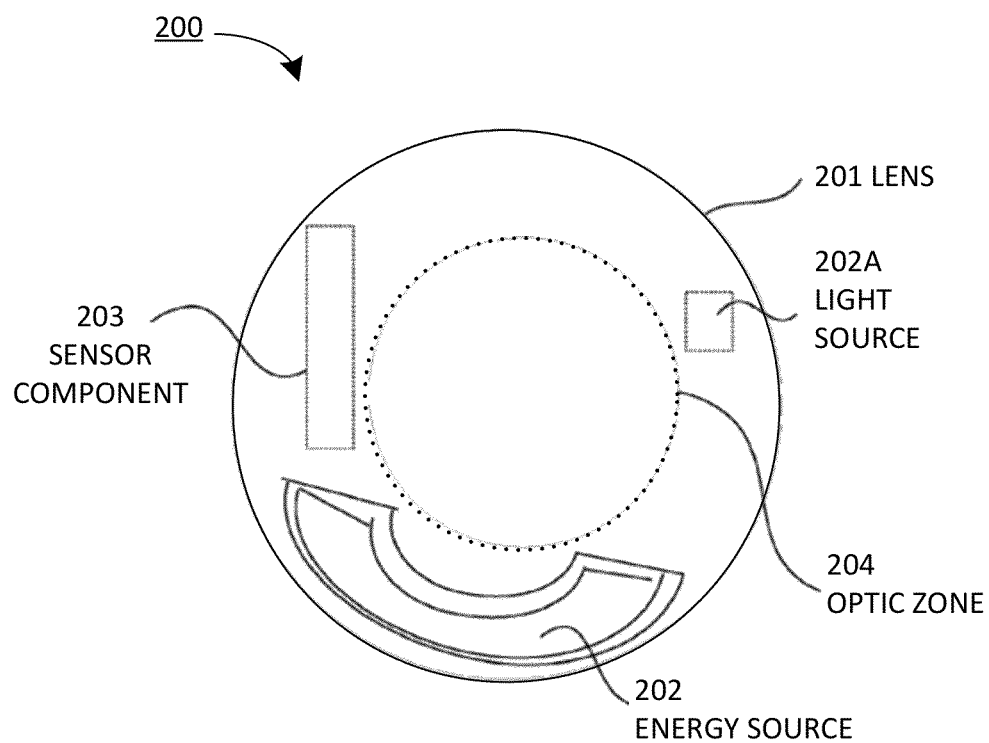
FIG. 2 illustrates an exemplary energized biomedical ophthalmic device with a biomarker sensor that may be used in some lens embodiments of the present invention.

Referring now to FIG. 2, an exemplary energized biomedical ophthalmic device with a biomarker sensor Component 203 that may be used in some energized ophthalmic lens 200 embodiments of the present invention is depicted. In addition to the biomarker sensor Component 203, the exemplary energized ophthalmic lens 200 comprises an Energy Source 202 and a Light Source 202A. The Energy Source 202 can be in electrical communication with a Light Source 202A and the Component 203. The Light Source 202A can include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. In another embodiment, a single Light Source may be piped to one or more locations in an ophthalmic lens 201 to provide the illumination required for SAD light therapy.

The Component 203 can include any light sensor and/or electrochemical sensor device with analytical sensitivity to detect changes in biomarkers. The component may include a microchip with electrophoresis and selective chemoluminescence capabilities including, for example, capability to detect changes in fluorescence, absorbance, light scatter or plasmon resonance of tear film, light exposure, and circadian rhythm. In some embodiments, Component 203 can react to an electrical change with a change in state and be, for example: a microchip such as a semiconductor type chip; a passive electrical device; an optical device such as a crystal lens; a processor with a micro-electromechanical machine (MEMS), or a nano-electromechanical machine (NEMS).

Moreover, the Component 203 can include or be in logical connection with an electrical storage device such as a capacitor; ultracapacitor; supercapacitor; or other storage component. An Energy Source 202 can include, for example: a lithium ion battery located in the periphery of an ophthalmic lens outside of the optic zone and be chargeable via one or more of radio frequency; photo voltaics, and magnetic inductance into an Energy Source 202.

As illustrated, in some embodiments, the Energy Source portion 202, the Light Source 202A, and the Component 203 can preferably be located outside of an Optic Zone 204, wherein the Optic Zone 204 includes that portion of the ophthalmic lens 200 providing a line of sight for an ophthalmic lens 200 wearer. Other embodiments may include an Energy Source 202 in the optic zone portion of an ophthalmic lens. For example, such embodiments can include an Energy Source 202 of conductive particles too small to be viewable without aid to the human eye.

In some embodiments, a preferred ophthalmic lens type can include a lens 201 that includes a silicone containing component. A "silicone-containing component" is one that contains at least one [—Si—O—] unit in a monomer, macromer or prepolymer. Preferably, the total Si and attached 0 are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Figure 3:
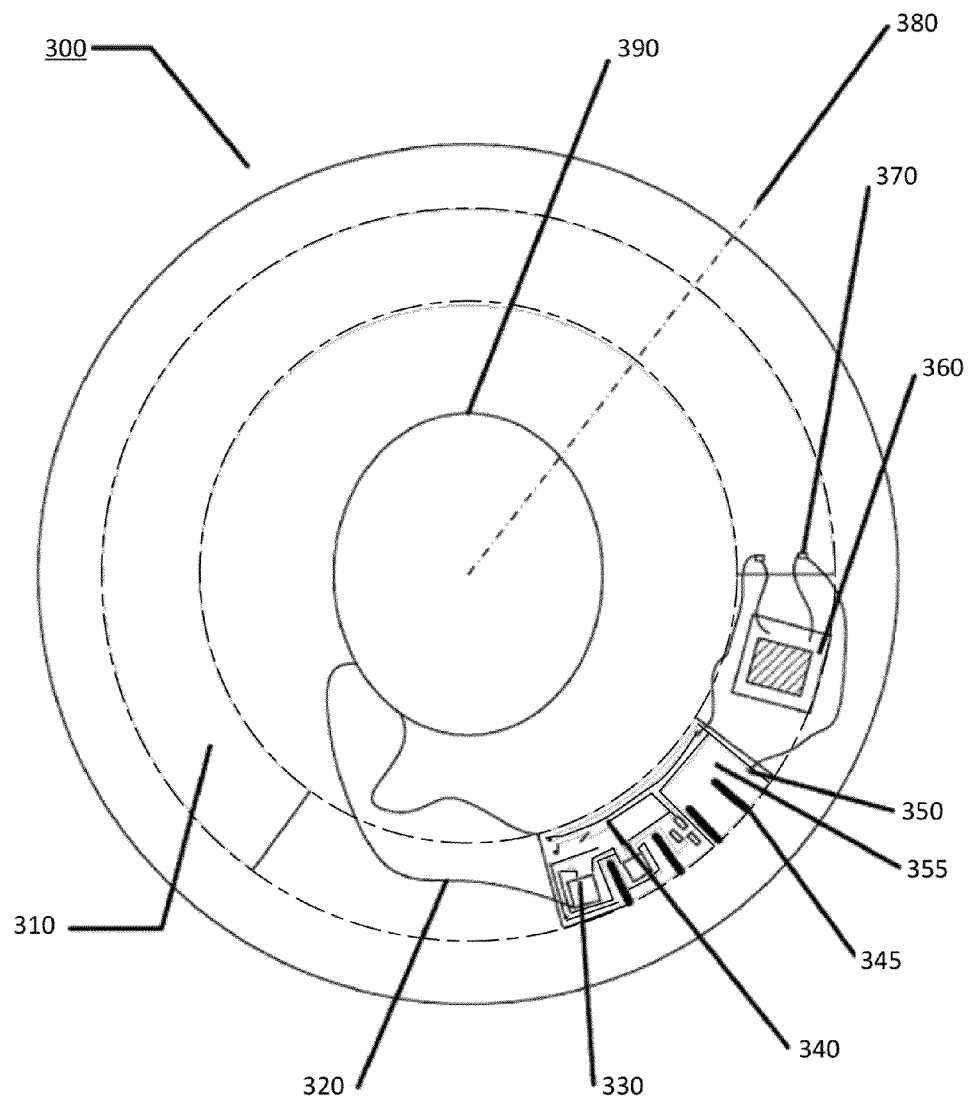
FIG. 3 illustrates an exemplary processor that may be used in some embodiments of the present invention.

Referring now to FIG. 3, an exemplary processor that may be used in some Energized Biomedical Ophthalmic Device embodiments of the present invention is illustrated at 300. In this illustration, the Energy Source 310 may include a thin film, rechargeable lithium ion battery. The battery may have contact points 370 to allow for interconnection. Wires may be wire bond wires to the contact points 370 and connect the battery to a photoelectric cell 360 which may be used to reenergize the battery Energy Source 310. Additional wires may connect the Energy Source to a flexible circuit interconnect via wire bonded contacts on a second set of contact points 350. These contact points 350 may be a portion of a flexible interconnect substrate 355 which may also include a Light Source 330.

The interconnect substrate may be formed into a shape approximating a typical lens conical form or other form depending on the Biomedical Ophthalmic Device. However to add additional flexibility needed in some embodiments, the interconnect substrate 355 may include additional shape features such as radial cuts 345 along its length. Radial cuts may be used to form individual flap shaped structured of the interconnect substrate 355 and may be connected various electronic Components like ICs, discrete Components, passive Components and such devices which are shown as item 390. Components can be interconnected by wires or other connection means 340 to the conduction paths within the interconnect substrate 355. By way of non-limiting example, the various components may be connected to the flexible interconnect substrate 355 by the various means of making interconnections to the battery. The combination of the various electrical Components may define a control signal for control of the biomarker monitoring, light source, and in some embodiments, for an electro-optical device shown as item 390. This control signal may be conducted respectively along interconnect 320.

This type of exemplary energized ophthalmic lens with energized functions is provided only for the purpose of example. In no way should this description be construed to limit the scope of the inventive art as it will be apparent to one skilled in the art that many different embodiments of function, design, interconnection scheme, energization scheme and overall utilization of the concepts of this invention may exist from this disclosure. For example, in some embodiments there may be manners of affecting the ophthalmic lens' appearance. Aesthetics of the thin film microbattery surface may be altered in various manners which demonstrate a particular appearance when embedded in the electroactive contact lens or shaped hydrogel article. The thin film microbattery may be produced with aesthetically pleasing patterned and/or colored packaging materials which could serve to either give a muted appearance of the thin film microbattery or alternatively provide iris-like colored patterns, solid and/or mixed color patterns, reflective designs, iridescent designs, metallic designs, or potentially any other artistic design or pattern. In other embodiments, the thin film battery may be partially obscured by other Components within the lens, for example, a photovoltaic chip mounted to the battery anterior surface, or alternatively, by placement of the battery behind all or a portion of a flexible circuit. In further embodiments, the thin film battery may be strategically located such that either the upper or lower eyelid partially or wholly obscures the visibility of the battery.

In preferred embodiments, the Energy Source and Light Source may not obstruct the transmission of light through the ophthalmic lens. Consequently, designs can be so that the Optical Zone, central 5-8 mm, of the energized lens may not be significantly obstructed by any opaque portions of the Energy Source and Light Source. There may be many different embodiments relating to the design of various Energy Sources and Light Sources to interact favorably with the optically relevant portions of an energized ophthalmic lens.

According to some aspects of the present invention, the Energy Source and Light Source should be placed at a certain distance from the outer edge of the contact lens to enable advantageous design of the contact lens edge profile in order to provide good comfort while minimizing occurrence of adverse events. Examples of such adverse events to be avoided may include superior epithelial arcuate lesions or giant papillary conjunctivitis.

In some embodiments, a cathode, electrolyte and anode features of embedded electrochemical cells can be included and be formed, for example, by printing appropriate inks in shapes to define such cathode, electrolyte and anode regions. It may be apparent that batteries thus formed could include both single use cells, based for example on manganese oxide and zinc chemistries, and rechargeable thin batteries based on lithium chemistry thin film battery chemistry. It can also be apparent to one skilled in the art that a variety of different embodiments of the various features and methods of forming Energized Biomedical Ophthalmic Devices may involve the use of printing techniques.

Figure 4:
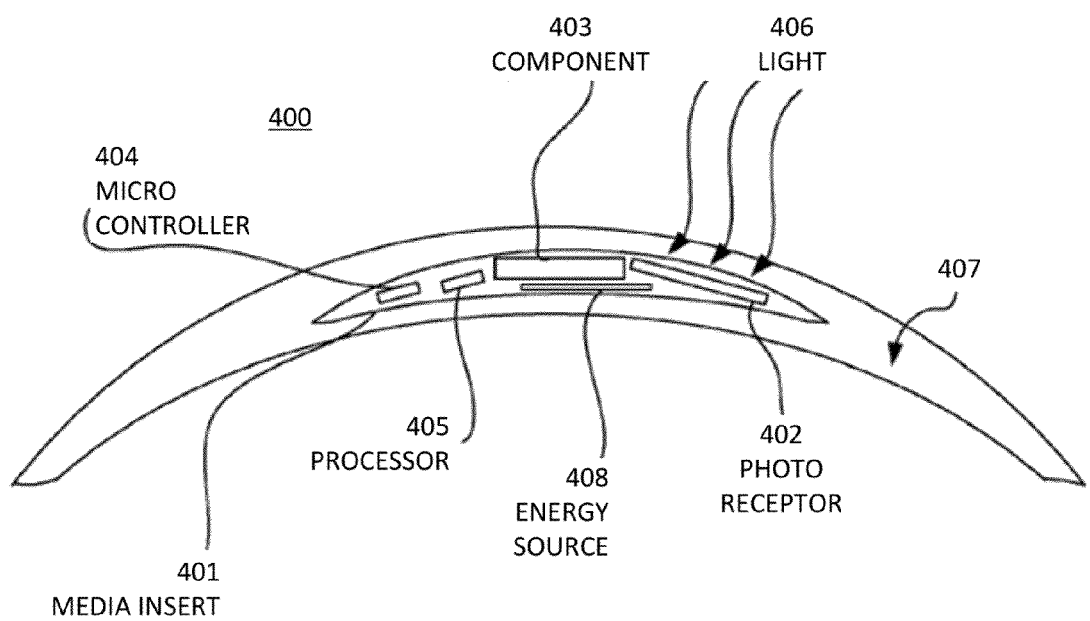
FIG. 4 illustrates an energized biomedical ophthalmic device with an exemplary media insert including a microcontroller that may be used in some lens embodiments of the present invention.

Referring now to FIG. 4, a cross section of an Energized Biomedical Ophthalmic Device 400 with an exemplary media insert 401 including a microcontroller 404 that may be used in some lens embodiments of the present invention is depicted. An activator or processor 405 can be used to implement one or more executable programs included within memory storage in the Microcontroller 404. Programs can be operative to control a light source (not shown) in logical communication with the Microcontroller. One or more Light Source may be included in the media insert, outside the media insert in/on the biomedical ophthalmic device, or in proximity thereto; for example, in complementary spectacles (further described in FIG. 6). Additionally, in some embodiments, a program executed via the Microcontroller 404 can cause a change of state in a Component 403. The memory storage can include a random access memory semiconductor; a read only memory semiconductor; a static memory; an erasable programmable read only memory; or other component capable of storing digital data and providing the data on command.

An Energy Harvester, such as a photoreceptor 402 can be included for recharging an Energy Source 408, such as a lithium based battery or a capacitor. The microcontroller 404 can be used to manage a Re-energizing process. For example, the processor 405 can receive data indicative of an amount of charge present in an energy source 408 and open a circuit allowing current to flow from an Energy Harvester 402, for example, a photoreceptor to the Energy Source 408 (other examples can include a magnetic or inductive device). In another aspect, the processor can also be programmed to monitor when the Energy Harvester 402 can be capable of providing sufficient current to charge an Energy Source 408 and provide an electrical pathway via circuitry suitable for such charging. Electrical circuitry for charging can include, for example, transistors acting as switches and diodes for ensuring a proper direction of current flow.

Figure 5:
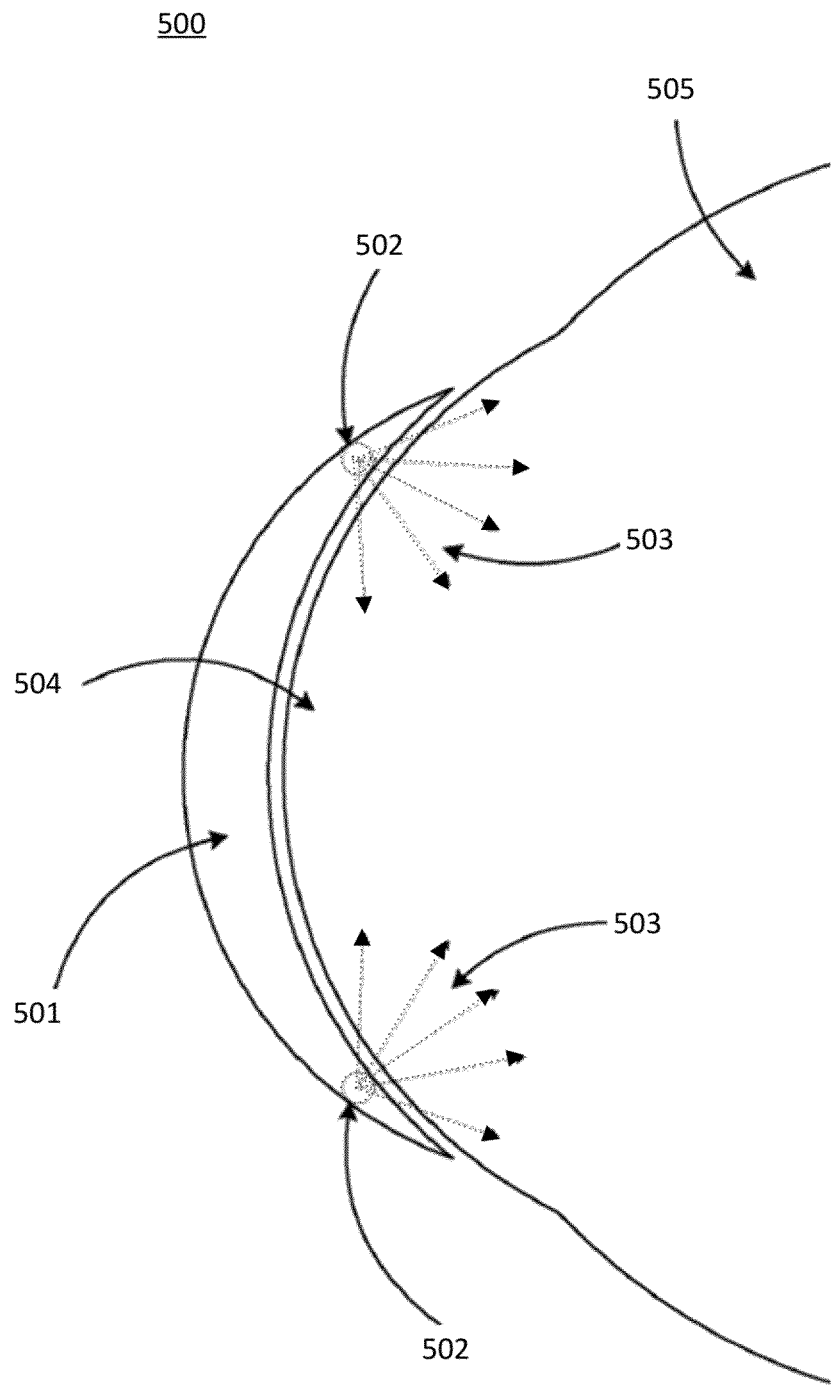
FIG. 5 illustrates a cross section view of an exemplary energized biomedical ophthalmic device containing light sources according to some lens embodiments of the present invention.

Referring now to FIG. 5, a cross section view of an exemplary energized biomedical ophthalmic device 500 containing light sources 502 according to some lens embodiments of the present invention is depicted. In the present example, the exemplary energized ophthalmic lens 501 is a contact lens and is depicted directing light 503 onto the cornea 504 of an eye 505. In some embodiments, a cross-section view 500 may be a top-down view, wherein one or more embedded Light Sources 502 are placed near the sides of a contact lens 501. In other embodiments, a cross-section view 500 may be a side view, such that one or more embedded Light Sources 502 are placed near the top and bottom of a contact lens 501. A number of Light Sources 502 and an arrangement of Light Sources 502 around a perimeter of a contact lens 501 may vary. A Light Source 502 directs illumination toward a wearer's eye such that illumination may not be obvious to an observer. A contact lens 501 may also include a coating which shields light therapy luminescence from being readily noticed by an observer to not diminish a user's Light Therapy.

Embedded Light Sources 502 can include light-emitting diodes (LEDs) or other Light Sources 502 capable of emitting light 1003 for Light Therapy. Light Sources 502 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. Another embodiment includes a single Light Source from which light may be piped to one or more locations within an ophthalmic lens 501 to provide illumination.

The exemplary ophthalmic lens 501 includes supporting electronics, not illustrated in this figure, with Components such as light sensors, biomarker sensors, Energy Source, capacitors, memory, processor, and communication device. Light sensors are used to detect ambient white light, blue light or green light. An Energy Source and capacitors can supply energy to other Components of an Energized Biomedical Ophthalmic Device. Memory may be used, by way of non-limiting example, to store pre-programmed Light Therapy Schedules, to store data collected from one or more sensors, to store user's preferences, to store actual Light Therapy dates, times, durations and intensities, and to store data related to a Light Source and light sensor operation in order to detect device failures. Moreover, a processor may be used, for example, to run programmed Light Therapy Schedules stored in memory, to analyze light sensor data and determine a unique personalized Light Therapy Schedule based on the wearer's exposure to ambient light, to evaluate manual changes to a programmed Light Therapy schedule and provide compensating adjustments, i.e., Intelligent Light Therapy, and to analyze light source and light sensor data to detect device failures.

A communication device may be used to electronically control one or more of: the transfer of digital data to and from an energized biomedical ophthalmic device and external devices, and the transfer of digital data between components within the energized biomedical ophthalmic device. The communication device may be used to wirelessly communicate with one or more external devices including, by way of non-limiting examples, a fob, a personal digital assistant (PDA), or a smartphone application used to control the Energized Biomedical Ophthalmic Device. Within Energized Biomedical Ophthalmic Devices, communication between Components may be via physical connection, such as via a direct conductive path, or may be wireless. Communication between internal components may include, for example, control of a Light Source from a processor and data transfer between sensors and memory.

Supporting electronics are in logical and electrical communication with Light Sources 502 contained within the energized biomedical ophthalmic device including, for example, a contact lens 501. Communication may be via a direct conductive path between supporting electronics and Light Sources 502 or via wireless communication. Wireless modes of communication may include, for example, inductance accomplished via an antenna located proximate to a Light Source 502 in the contact lens 501 and a power source transmitting power from another area within the contact lens 501 to the antenna.

In some embodiments, supporting electronics may be included in a fob, jewelry, hat, clothing, or other items worn by a user such that sensors, such as light sensors, detect ambient light experienced by the user and supporting electronics are near a contact lens for purposes of wireless communication. Wireless modes of communication can include, for example, inductance. Inductance may be accomplished via an antenna located in/on the energized biomedical ophthalmic device and a power source transmitting power from supporting electronics in jewelry, clothing, or other item proximate to the antenna.

In some embodiments, a user may adjust timing, duration and intensity of light therapy using an external device, including but not limited to one or more of: a fob, a personal digital assistant, computer, tablet, and a Smartphone application. Some embodiments provide for a basic operational state, wherein Light Therapy is controlled manually by a user starting and stopping therapy at appropriate times.

According to the present embodiment, a programmed Light Therapy Schedule may, for example, automatically adjust light therapy timing, duration and intensity based on variables such as, dates, geographic region, user's preferences, and biomarkers sensor collected data correlated to SAD symptoms and the severity of a user's SAD symptoms. A Programmed Light Therapy Schedule may be set by an eye care professional, a medical doctor, or a user. In some embodiments, the light therapy schedule may learn from past responses and adjust to provide Intelligent Light Therapy. For example, an response during programmed light therapy can include, a user adjusting light intensity based on an activity, such as, for example, decreasing light intensity when reading, working on a computer, or driving. Conversely, it may be desirable to increase light intensity during work breaks, lunch break, or other less visually active times. Accordingly, in some embodiments Intelligent Light Therapy can be delivered when a processor evaluates manual changes and detected user changes of a programmed Light Therapy Schedule and provides compensating adjustments in duration, frequencies and/or intensity of treatment. Intelligent Light Therapy can also be achieved when data from light sensors is analyzed by a processor and a programmed Light Therapy Schedule is dynamically adjusted based on a wearer's exposure to ambient light.

In another embodiment of the present invention, a user may manually adjust light therapy based on the results of tear fluid measured data, and/or blood, saliva testing including but not limited to testing for concentration of one or more of: melatonin, serotonin and interleukin-6 levels. Concentration of biomarkers can increase or decrease based on light exposure or a SAD symptom. For example, melatonin levels are inhibited by light and increase with darkness. Higher levels of melatonin promote sleepiness and lethargy, symptoms of seasonal affective disorder.

In still other embodiments, as part of an user's preferences, a user may manually adjust light therapy to intentionally alter their sleep cycle. The use of light therapy for sleep cycle alteration may be valuable for persons working night shifts, for persons travelling to significantly different time zones, for military personnel preparing for night operations, and other uses. Similarly, Light Therapy initiated by the user upon awakening may be used to treat circadian rhythm disorders such as delayed sleep phase syndrome (DSPS) and non-24-hour sleep-wake syndrome.

Figure 6:
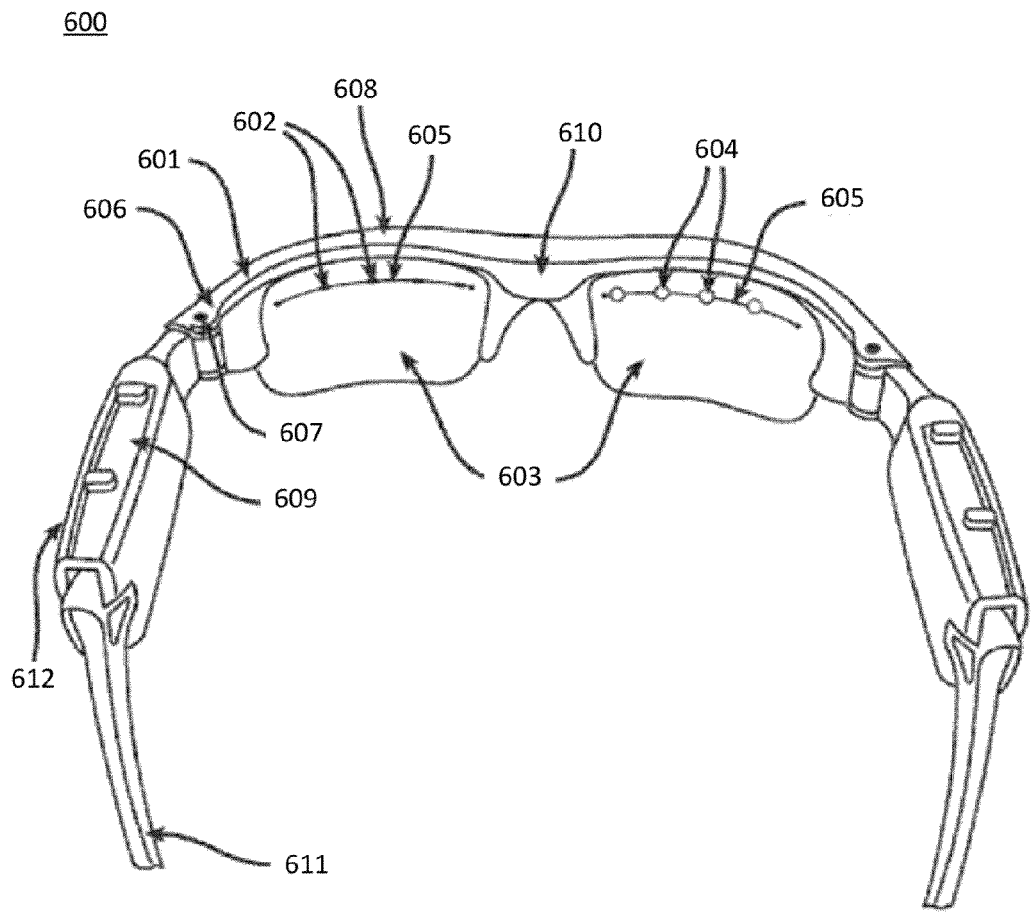
FIG. 6 illustrates the back view of exemplary complementary eyeglasses with light sources embedded in the lenses and with supporting electronics that may be used with some embodiments of the present invention.

Referring now to FIG. 6, the back view of exemplary eyeglasses 600 with light sources 602 embedded in the lenses 603 and with supporting electronics is depicted. In other embodiments, Light Sources 602 may also be mounted on the surface of lenses 603. Light Sources 602 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. In yet another embodiment, a single light source may be piped to one or more locations within an eyeglass lens 603 or eyeglass frame 601 to provide illumination. Light pipes may include, for example, fiber optic pathways.

An example of illuminated light sources is illustrated at 604. A light source 602 provides illumination toward a wearer's eyes such that an illumination is not obvious to an observer.

Light Sources 602 can be connected to one another via conductive paths 605. Conductive paths 605 may be wires embedded within a lens 603 or may be a conductive material including, for example, gold, copper, silver or other metal or conductive fiber applied to a surface of a lens 603 via pad printing, sputter coating, vapor deposition or another suitable method. Conductive paths 605 can be in electrical and logical communication with supporting electronics contained within one or both temple pieces 609. In some embodiments, supporting electronics are miniaturized such that they may be contained in other areas of eyeglasses such as in areas near a hinge 607, within a frame above a lens 608, within a bridge 610, within an earpiece 611, or other area.

One or more light sensors 606 can be used to detect ambient white light, blue light or green light. Light sensors 606 may be located within an eyeglass frame 601 near a hinge 607, within a frame above a lens 608, within a temple piece 609, within a bridge 610, or other appropriate area where a sensor 606 will not be obstructed, for example, by hair. A light sensor 606 is in electrical and logical communication with supporting electronics contained within one or both temple pieces 609 or other area of eyeglasses.

In some embodiments, a user control element 612, such as a switch or button, can be provided to allow a user to adjust timing, duration and intensity of light therapy. One or more user control elements 612 may be present in temple pieces 609 or other areas of eyeglasses including, for example, in areas near a hinge 607, within a frame above a lens 608, within a bridge 610, within an earpiece 611, or other area.

Figure 7:
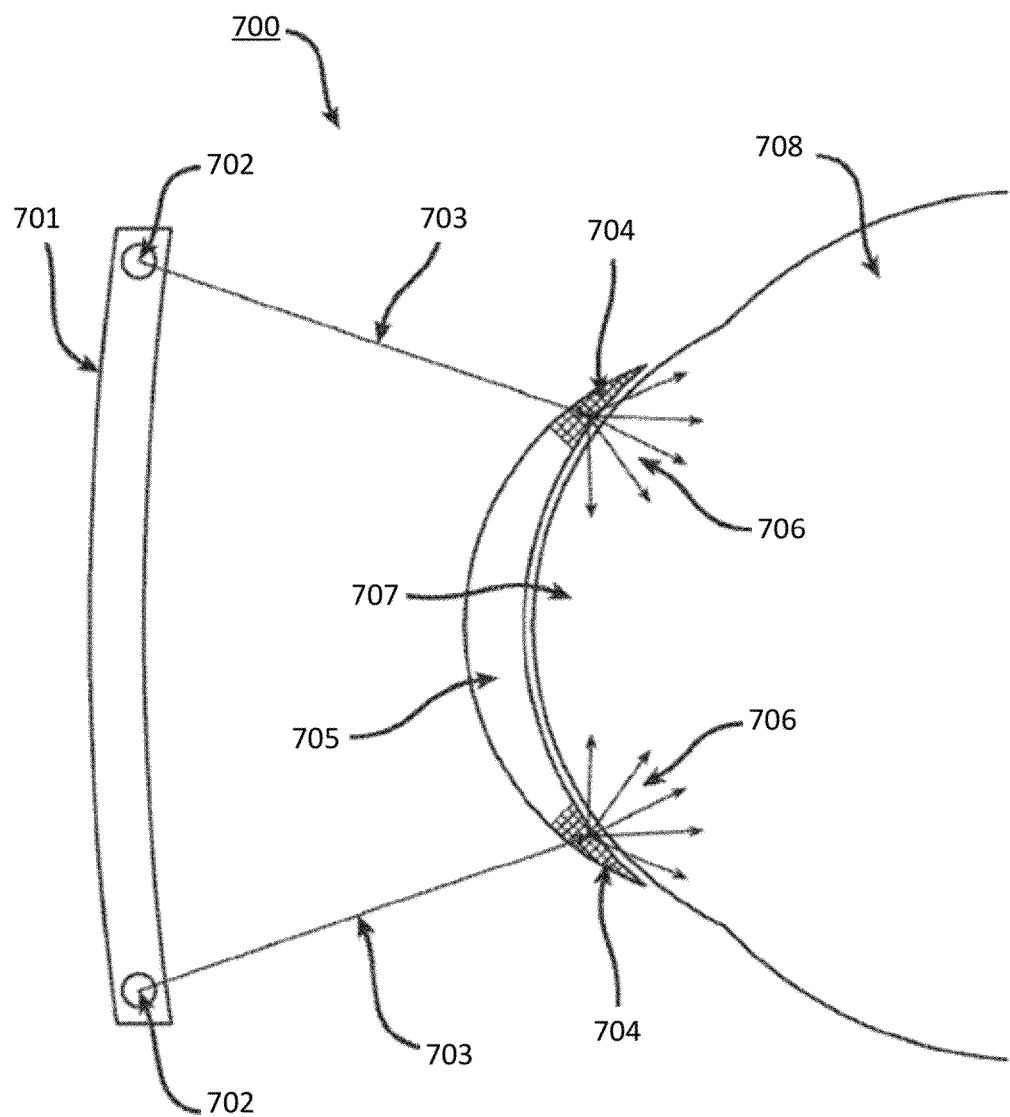
FIG. 7 illustrates a cross-section view of exemplary complementary eye glasses with embedded light sources directing light into an energized biomedical ophthalmic device according to some contact lens embodiments of the present invention.

Referring now to FIG. 7, a cross-section view 700 of exemplary eye glasses 701 with embedded light sources 702 directing light into a complementary energized biomedical ophthalmic device 705 according to some contact lens embodiments of the present invention is depicted. Cross-section view 700 includes an eyeglass lens 701 with embedded light sources 702 directing light 703 into light scattering areas 704 of a complementary contact lens 705. A light scattering area 704 can result in light 706 being dispersed across a cornea 707 of an eye 708. A light scattering area 704 may include diffractive properties, refractive properties, reflective properties or any combination of diffractive, refractive and reflective properties.

In some embodiments, a cross-section view 700 may be a top-down view, wherein one or more embedded light sources 702 are placed near the sides of an eyeglass lens 701. In other embodiments, a cross-section view 700 may be a side view, such that one or more embedded light sources 702 are placed near the top and bottom of an eyeglass lens 701. In still other embodiments, embedded light sources 702 may be embedded in or mounted on an eyeglass frame rather than an eyeglass lens 701.

Embedded light sources 702 can include, for example, the light-emitting diodes (LEDs) or other light sources 702 previously described herein. Supporting electronics (not shown) can be contained in an eyeglass frame and in the energized biomedical ophthalmic device and be in communication with each other. For example, for the biomarker sensor of the energized biomedical ophthalmic device to send collected biomarker concentration data to a communication Component of the eyeglasses. Supporting electronics can be Components located in one or the complementary devices of both, and may include components including, for example, light sensors, batteries, capacitors, memory, processors, and a USB connector. Moreover, supporting electronics are in logical and electrical communication with light sources 702 and biomarker sensors (not depicted). Electrical communication may be provided, for example, via a conductive contact between a source located in a temple of a pair of eyeglasses, via a conductive wire, a conductive ribbon wire, or via wireless modes, such as inductance. Inductance may be accomplished, for example, between an antenna located in the eyeglasses and complementary lens.

In some embodiments, light scattering areas 704 of a complimentary contact lens 705 form a ring within a perimeter area of a complimentary contact lens 705 such that directed light 703 need not strike a limited target area. The orientation of a complimentary contact lens 705 on an eye 708 relative to light sources 702 within an eyeglass lens 701 is therefore inconsequential when light 703 is directed toward a light scattering area 704 continuously present around a perimeter area of a complimentary contact lens 705.

In some preferred embodiments, a complimentary contact lens 705 may include an internal barrier between a light scattering area 704 and an Optical Zone in a central portion of a lens. An internal barrier prevents light 703 intended for light therapy from being dispersed into an Optical Zone of a complimentary contact lens 705. This way, light 703 intended for Light Therapy is only dispersed around a perimeter of a cornea 707, minimizing its effect on normal vision.

In still other embodiments, an entire complimentary contact lens 705 includes light scattering properties such as diffraction, refraction and reflection. Light scattering properties are designed such that they disperse only light 703 of wavelengths emitted by embedded light sources 702. This embodiment supports maximum dispersion of light 703 wavelengths intended for Light Therapy within an eye 708 while not causing dispersion of light wavelengths that would affect normal vision.

Figure 8:
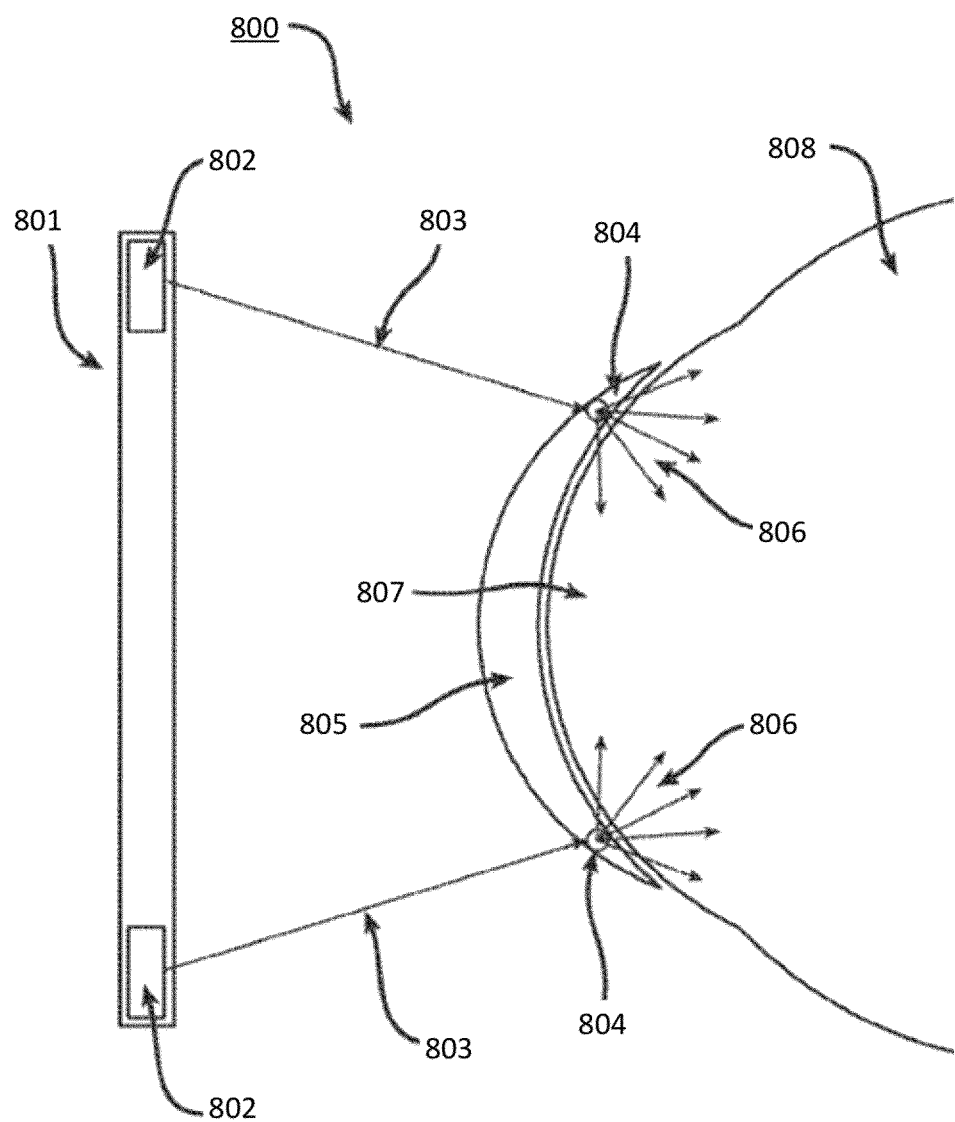
FIG. 8 illustrates a cross-section view of exemplary complementary eyeglasses with supporting electronics in wireless communication with an energized biomedical ophthalmic device containing light sources according to some contact lens embodiments of the present invention.

Referring now to FIG. 8, a cross-section view 800 of exemplary eye glasses 801 with supporting electronics 802 in wireless communication with an energized biomedical ophthalmic device 805 containing light sources 804 according to some contact lens embodiments of the present invention is depicted. Cross-section view 800 includes an eyeglass frame 801 containing supporting electronics 802. Supporting electronics 802 may include Components such as light sensors, batteries, capacitors, memory, processors, and a USB connector. Supporting electronics 802 are in wireless communication 803 with a complimentary contact lens 805 containing embedded Light Sources 804 directing light 806 onto a cornea 807 of an eye 808. Supporting electronics 802 may be placed in various locations embedded in or mounted on an eyeglass frame 801.

In other embodiments, supporting electronics 802 may be included in jewelry, hats, clothing, or other items worn by a user such that light sensors detect ambient light experienced by the user and supporting electronics 802 are near a complimentary contact lens 805 for purposes of wireless communication. Wireless modes of communication may include, for example, inductance. Inductance may be accomplished via an antenna located in a complimentary contact lens 805 and a power source transmitting power from an eyeglass frame 801, jewelry, clothing, or other item proximate to the antenna.

In some embodiments of the present invention, a cross-section view 800 may be a top-down view, wherein supporting electronics 802 are placed near the sides of an eyeglass frame 801. In other embodiments, a cross-section view 800 may be a side view, such that supporting electronics 802 are placed near the top and bottom of a side of an eyeglass frame 801. A number of embedded light sources 804 and an arrangement of embedded light sources 804 around a perimeter of a complimentary contact lens 805 may vary. Embedded light sources 804 include previously described light-emitting diodes (LEDs) or other light sources 804 emitting light 806 for light therapy.

In some embodiments, Light Sources 804 may direct light 806 into an interior portion of a complimentary contact lens 805 in which the Light Sources 804 can be embedded or positioned onto a surface of the contact lens. Light 806 may be directed into a light scattering area, not depicted, including diffractive properties, refractive properties, reflective properties, or any combination of diffractive, refractive and reflective properties. A light scattering area may form a ring within a perimeter area of a complimentary contact lens 805. Light 806 striking a light scattering area causes a generally broad dispersion of light 806 onto a cornea 807 of an eye 808.

In some preferred embodiments, a complimentary contact lens 805 may also include an internal barrier between a light scattering area around a perimeter of a lens and an optical zone in a central portion of a lens, and light scattering properties as previously described.

Antennas or antenna systems may serve as a means for receiving signals, as a means for transmitting signals, as an inductive coupling means, or any combination thereof. The function of an antenna determines its design as well as its supporting circuitry. For example, an antenna may be coupled to a receiver unit, a transmitter circuit, an inductive coupling circuit or to any combination thereof. Basically, an antenna is an electrical device that converts electromagnetic waveforms, or electrical signals into different electrical signals. The discussion of FIG. 9A and FIG. 9B focuses on exemplary assemblies that comprise antenna systems and FIG. 9C represents a block diagram of an antenna and receiver circuit in accordance to the exemplary assemblies of FIGS. 9A and 9B.

Referring now to FIG. 9A, an exemplary antenna system according to some embodiments of the present invention is depicted. Circuit board 904A that may be utilized with one or more Component of the energized biomedical ophthalmic device, such as the biomarker sensor, Light Source and/or an optical lens assembly of an ophthalmic lens. Circuit board 904A comprises both top side conductive interconnect traces 912A1 and bottom side conductive interconnected traces 912A2 (shown in phantom), through-holes or vias 918A for making electrical connections between the top and bottom sides, mounting pads 914A, a center opening 916A, and one or more spiral antenna structures 920A. However, in some embodiments, a single loop antenna may be appropriate. Each of the one or more spiral antenna structures 920A can comprise one or more turns of wire, conductive traces or the like formed in either or both of the top side or the bottom side of the circuit board 904A. If multiple antennas are utilized on opposite sides, the through-hole or vias 908A may be utilized to make connections therebetween.

It will be appreciated that the circuit board 904A may comprise additional metal layers and that any combination of layers may be used to construct the spiral antenna structures 920A. The antenna structures alternately may be embedded on an inner conducting layer, with other conducting layers above and/or below the antenna structures 920A.

Referring now to FIG. 9B, another exemplary antenna system according to some embodiments of the present invention is depicted. Like the previous example, circuit board 904A that may be utilized with one or more Component of the Energized Biomedical Ophthalmic Device, such as the biomarker sensor, Light Source and/or an optical lens assembly of an ophthalmic lens. Circuit board 904B comprises both top side conductive interconnect traces 912B1 and bottom side conductive interconnected traces 912B2 (shown in phantom), through-holes or vias 918B for making electrical connections between the top and bottom sides, mounting pads 914B, a center opening 916B, and a multi-turn loop antenna 920B. However, in some embodiments a single loop antenna may be appropriate. The multi-loop antenna 920B comprises two or more turns of wire, conductive traces or the like formed in either or both of the top side or the bottom side of the circuit board 904B. If multiple antennas are utilized on opposite sides, the through-hole or vias 908B may be utilized to make connections therebetween. It will be appreciated that the circuit board 904B may comprise additional metal layers and that any combination of layers may be used to construct the multi-turn loop antenna 920B.

Before the description of an exemplary block diagram of an antenna and receiver circuit, it is important to note that the circuits set forth and described subsequently may be implemented in a number of ways. In one exemplary embodiment, the circuits may be implements using discrete analog components. In another exemplary embodiment, the circuits may be implemented in integrated circuits or a combination of integrated circuits and discrete components. In yet another alternate exemplary embodiment, the circuits or particular functions may be implemented via software running on a microprocessor or microcontroller.

Referring now to FIG. 9C, a block diagram representation of an antenna and receiver circuit in accordance to some embodiments of the present invention is illustrated. The radio receiver electronic circuit 900C can comprise an antenna match circuit 904C, a receiver circuit 906C, a controller 908C, an actuator 910C, a battery 912C and a power management circuit 914C. In this exemplary configuration, the antenna 904C can be adapted to receive an electromagnetic signal 901C and to provide a received electrical signal to the antenna match circuit 904C. The antenna match circuit 904C may comprise any suitable circuitry necessary for balancing the impedance between the source and the load to maximize power transfer and/or minimize reflection from the load. Essentially, antenna impedance is the ratio of voltage to current at any point on the antenna and for efficient operation, the antenna impendence should be matched to the load, and thus a match circuit is utilized.

Accordingly, the match circuit 904C can be adopted to provide an impedance match between the antenna 902C and the receiver circuit 906C for an optimum power match, noise match or other match condition as is known in the radio and circuit design arts. The receiver circuit 906C can comprise any suitable circuitry necessary to process the modulated signal received by the antenna 902C and provide a demodulated signal to the controller 908C. For purposes of clarity, modulation involves varying one or more properties of a signal or electromagnetic waveform. For example, a waveform may be amplitude (AM), frequency modulated (FM) or phase modulated (PM). Other forms of analog as well as digital modulation can also be implemented in some embodiments.

Demodulation, on the other hand, can include extracting the original information bearing signal from the modulated carrier wave. It is this demodulated information signal that can provide instructions to the controller 908C. The controller 908C in turn can provide a control signal to the actuator 910C based upon the demodulated signal in order to control a state or operation of the actuator 910C. The control signal may be further based on any internal state of the controller, for example, to implement control laws, and/or any other circuits coupled to the controller, for example, to implement a feedback control system or to modify the actuator operation based on other information such as information based upon sensor data.

The battery 912C provides a source of electrical energy for Components in the electronic circuit 900C requiring energy. The power management circuit 914C can be adapted to receive a current from the battery 912C and condition it or regulate it to provide a workable output voltage suitable for use by the other active circuits in the electronic circuit 900C. The controller 908C may also be utilized to control the receiver circuit 906 or other circuits in the receiver 900C. The antenna 902C may comprise, for example, one or more of the configurations previously described. Other embodiments may include single turn loop antenna, a multi-turn loop antenna, a spiral antenna, a coil antenna subassembly, a stacked die configuration or arrangement or a suitable combination thereof.

As is known in the relevant art, a preferred method for the transfer of power between an antenna and a receiving and/or transmitting circuit may require matching the impedance presented and/or transmitting circuit requires matching the impedance presented to the antenna and the impedance presented to the circuit. Essentially, suitable power transfer can occur when the reactive components of the antenna and circuit impedance are cancelled and the resistive components of the impedances are equal. A matching circuit may be introduced to couple the antenna to the circuit that meets the optimum power transfer criterion at each, thereby allowing for optimum power transfer to occur between the antenna and circuit. Alternatively, a different criterion may be selected to optimize a different parameter such as maximum current or voltage at the circuit. Matching circuits are well known in the art and may be implemented with discrete circuit component such as capacitors, inductors and resistors, or with conductive structures such as traces in a circuit board, that provide a desired impendence characteristic.

Impedances of small RF loop antennas are typically between 20 and 50 nanohenries, and matching component valves can be in the range of 0.5 to 10 picofarads for capacitors and 3 to 50 nanohenries for inductors. Impedances of inductive charging coils are typically between 100 nanohenries and 5 nanohenries and associated capacitors for resonating the circuits are between 20 and 100 picoforads.

The actuator 910C may comprise any number of suitable devices. For example, the actuator 910C may comprise any type of electromechanical device, for example, a pump or transducer. The actuator may also comprise an electrical device, a chemical release device or any combination thereof. The actuator 910C may be replaced or include a controlled device, for example, a Light Source used to deliver Light Therapy, or diode array or any other suitable display, or user interface.

The battery 912C may comprise any suitable device for the storage of electrical energy as previously described. In alternate exemplary embodiments, no battery may be required as explained above with respect to RF energy harvesting or near field inductive coupling. Alternatively, mechanical vibration and similar means may be utilized to generate or harvest power.

The power management circuit 914C may comprise additional circuitry for a wide variety of functions in addition to regulating the output of the battery 912C. For example, the power management circuit 914C may comprise circuitry for monitoring various battery parameters such as charge, preventing overdischarge of the battery, and/or supervising the startup and shut down of the electronic circuit 900C.

Figure 10:
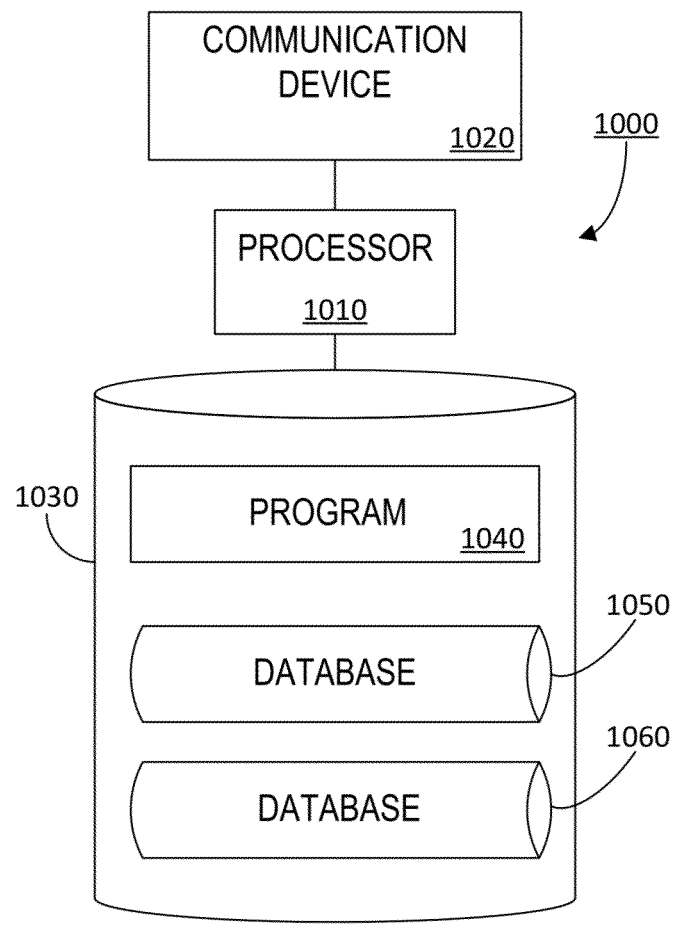
FIG. 10 is a schematic diagram of a processor that may be used to implement some embodiments of the present invention.

Referring now to FIG. 10, the block diagram of a controller 1000 that may be used to implement some embodiments of the present invention is depicted. The controller 1000 includes a processor 1010, which may include one or more processor components coupled to a communication device 1020. In some embodiments, a controller 1000 can be used to transmit energy to an Energy Source, sensor, and/or Light Source placed in an energized biomedical ophthalmic device.

The controller can include one or more processors, coupled to a communication device configured to communicate energy via a communication channel. The communication device may be used to electronically control the transfer of digital data to and from an ophthalmic device and/or control of a Light Source or other component incorporated into the ophthalmic lens.

The communication device 1020 may also be used to communicate, for example, with one or more controller apparatus or manufacturing equipment components. The processor 1010 is also in communication with a storage device 1030. The storage device 1030 may comprise any appropriate information storage device, including combinations of magnetic storage devices, optical storage devices, and/or semiconductor memory devices such as Random Access Memory (RAM) devices and Read Only Memory (ROM) devices.

The storage device 1030 can store a program 1040 for controlling the processor 1010. The processor 1010 performs instructions of the program 1040, and thereby operates in accordance with the present invention. The storage device 1030 can also store data, such as, ophthalmic data, geographic data, sensor data, and related data in one or more databases. The database may include customized Energy Source and Light Source designs, and specific control sequences for controlling energy to and from an Energy Source, sensor, and a Light Source.

CONCLUSION

A number of embodiments of the present invention have been described. While this specification contains many specific implementation details, there should not be construed as limitations on the scope of any inventions or of what may be claimed, but rather as descriptions of features specific to particular apparatus embodiments of the present invention.

Certain apparatus and Lens features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while method steps are depicted in the drawings in a particular order, this should not be understood as requiring that such method steps be performed in the particular order shown or in sequential order, or that all illustrated operations be performed, to achieve desirable results. In certain circumstances, multitasking and parallel may be advantageous. Moreover, the separation of various apparatus components in the embodiments described above should not be understood as requiring such separation in all embodiments, and it should be understood that the described apparatus components and method steps can generally be integrated together in a single apparatus or method or used in multiple apparatus or methods.

Thus, particular embodiments of the subject matter have been described. Other embodiments are within the scope of the following claims. In some cases, the method steps recited in the claims can be performed in a different order and still achieve desirable results. In addition, the processes depicted in the accompanying figures do not necessarily require the particular order show, or sequential order, to achieve desirable results. Nevertheless, it will be understood that various modifications may be made without departing from the spirit and scope of the claimed invention.

The invention claimed is:

1. An energized biomedical ophthalmic device capable of residing in or on an eye of a user, comprising:
    a body selected from the group consisting of an energized contact lens, intraocular lens, overlay lens, ocular insert and punctal plug, wherein the body comprises:
        an energy source;
        a light source configured to emit light for the treatment of a seasonal affective disorder of the user, energized by the energy source and positioned to direct the light towards the eye of the user;
        a biomarker sensor configured to detect changes in biomolecules contained in the tear film of the user and generate signal data corresponding to the detected changes, wherein the biomolecules are selected from the group consisting of serotonin, melatonin and Interleukin-6;
        a processor in logical communication with the biomarker sensor, wherein the processor is configured to receive and process said signal data and to control the light source.

2. The energized biomedical ophthalmic device of claim 1, additionally comprising a light sensor in communication with the processor.

3. The energized biomedical ophthalmic device of claim 1, wherein the biomarker sensor comprises an electrochemical microchip with analytical sensitivity.

4. The energized biomedical ophthalmic device of claim 3, wherein the electrochemical microchip with analytical sensitivity is configured to measuring changes of melatonin biomolecules in tear film.

5. The energized biomedical ophthalmic device of claim 3, wherein the electrochemical microchip with analytical sensitivity is configured to measuring changes of serotonin biomolecules in tear film.

6. The energized biomedical ophthalmic device of claim 3, wherein the electrochemical microchip with analytical sensitivity is configured to measuring changes of interleukin-6 biomolecules in tear film.

7. The energized biomedical ophthalmic device of claim 1, wherein the body is an energized contact lens.

8. The energized biomedical ophthalmic device claim 7, wherein the energized contact lens comprises a media insert encapsulating the energy source.

9. The energized biomedical ophthalmic device claim 1, additionally comprising an antenna.

10. The energized biomedical ophthalmic device claim 9, wherein the antenna can transmit electrical signals from an exterior controller.

11. The energized biomedical ophthalmic device claim 1, wherein the light source comprises one or more light-emitting diodes.

* * * * *